(12) United States Patent
Mosler et al.

(10) Patent No.: US 7,429,271 B2
(45) Date of Patent: Sep. 30, 2008

(54) CLAMPING FREEWHEEL AND ITS USE FOR A PROSTHETIC PART

(75) Inventors: Lueder Mosler, Duderstadt (DE); Martin Hillmann, Duderstadt (DE)

(73) Assignee: Otto Bock HeathCare IP GmbH & Co., KG, Duderstadt (DE)

( * ) Notice: Subject to any disclaimer, the term of this patent is extended or adjusted under 35 U.S.C. 154(b) by 196 days.

(21) Appl. No.: 11/220,417

(22) Filed: Sep. 7, 2005

(65) Prior Publication Data

US 2006/0049019 A1 Mar. 9, 2006

(30) Foreign Application Priority Data

Sep. 8, 2004 (DE) .................. 10 2004 043 805

(51) Int. Cl.
*A61F 2/80* (2006.01)
*F16D 41/064* (2006.01)
(52) U.S. Cl. .................. 623/36; 192/223.2; 192/45; 403/325
(58) Field of Classification Search ............... 192/223.2
See application file for complete search history.

(56) References Cited

U.S. PATENT DOCUMENTS

| 1,680,618 | A | * | 8/1928 | Hutton | ..................... 192/223.2 |
| 3,279,571 | A | | 10/1966 | Wassilieff | |
| 6,152,645 | A | * | 11/2000 | Sanford | ..................... 403/328 |
| 6,267,787 | B1 | | 7/2001 | Capper et al. | ..................... 623/36 |
| 7,217,060 | B2 | | 5/2007 | Ingimarsson | ..................... 403/325 |
| 2005/0216096 | A1 | * | 9/2005 | Wagman | ..................... 623/38 |
| 2005/0244220 | A1 | * | 11/2005 | Ingimarsson | ..................... 403/344 |

FOREIGN PATENT DOCUMENTS

| AU | 125797 | 12/1931 |
| DE | 605879 | 11/1934 |
| DE | 874684 | 4/1953 |
| JP | 2004-125140 | 4/2004 |
| WO | PCT/DE98/01979 | 7/1998 |
| WO | WO 2006/076011 A1 | 4/2005 |

* cited by examiner

*Primary Examiner*—Richard M. Lorence
(74) *Attorney, Agent, or Firm*—Whitham Curtis Christofferson & Cook, PC

(57) ABSTRACT

In a clamping freewheel having a sleeve (5) which encloses a shaft (7, 9) and in which the shaft (7, 9) is mounted in an axially displaceable manner, having rolling elements (6) which are arranged in chambers, formed between shaft (7, 9) and sleeve (5), in such a way that they roll in a first direction for a relative rotation between shaft (7, 9) and sleeve (5), whereas a torque acting in the opposite direction leads to the clamping of the rolling elements (6) in their chamber, having a transmission element (11) arranged on the shaft (7, 9), and having an actuating element (16) for the axial displacement of the transmission element (11) arranged on the shaft (7, 9), the function of the axial displacement is separated from the function of the clamping by virtue of the fact that the shaft (7, 9) consists of a hollow shaft piece (7) and an inner piece (9) axially displaceable therein, but mounted in a rotationally locked manner, and that the actuating element (16) and the transmission element (11) are arranged on the inner piece (9). As a result, the initiation of the axial displacement becomes independent of the clamping forces.

Figure 3:
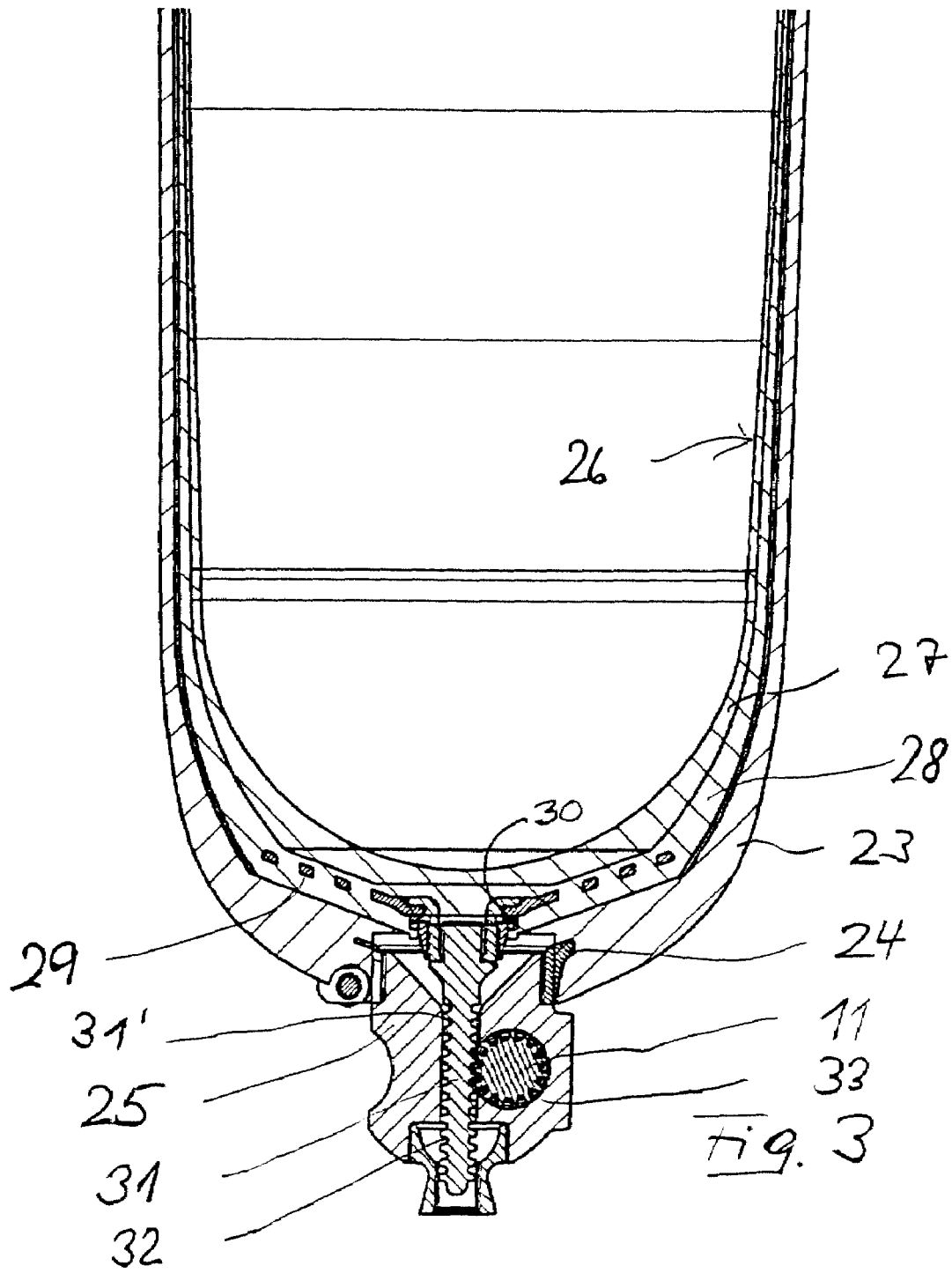

A preferred field of application of the clamping freewheel consists in locking a linearly movable prosthetic part.

8 Claims, 3 Drawing Sheets

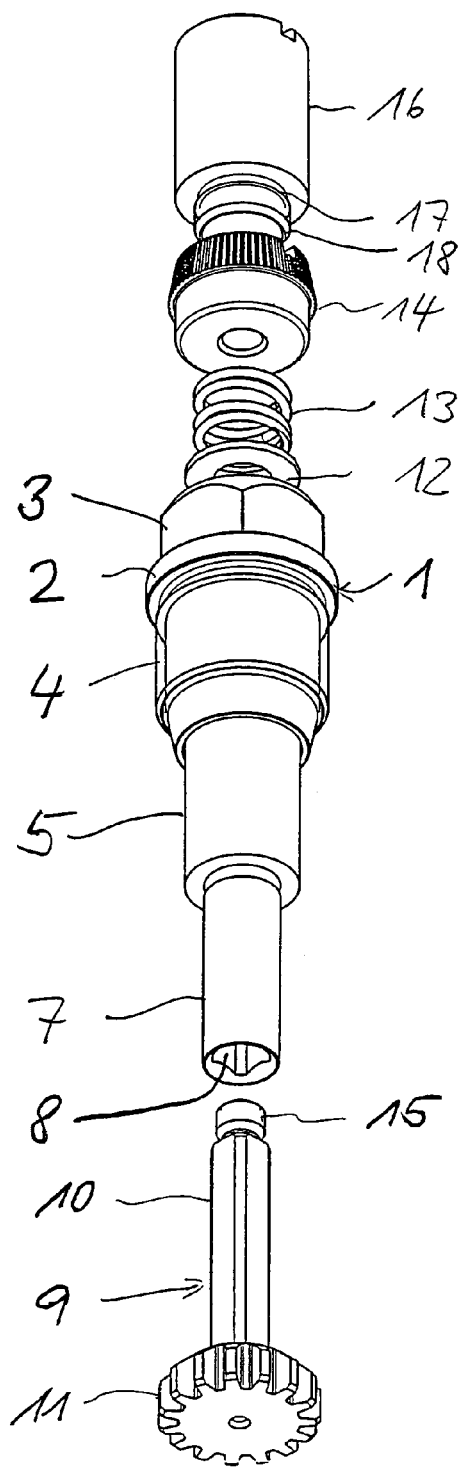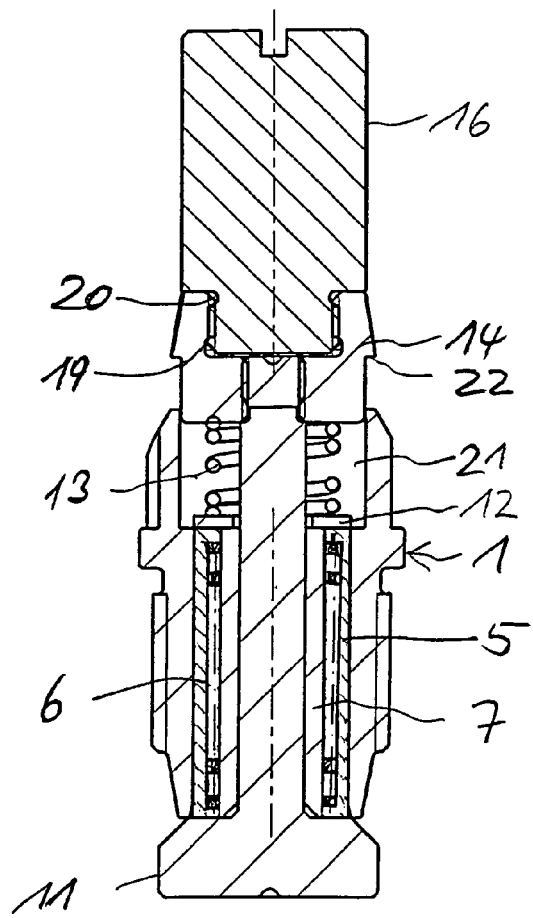
Fig. 1
Fig. 2

CLAMPING FREEWHEEL AND ITS USE FOR A PROSTHETIC PART

The invention relates to a clamping freewheel having a sleeve which encloses a shaft and in which the shaft is mounted in an axially displaceable manner, having rolling elements which are arranged in chambers, formed between shaft and sleeve, in such a way that they roll in a first direction for a relative rotation between shaft and sleeve, whereas a torque acting in the opposite direction leads to the clamping of the rolling elements in their chamber, having a transmission element arranged on the shaft, and having an actuating element for the axial displacement of the transmission element arranged on the shaft.

Such clamping freewheels are known as standard components and produce the lowest possible resistance for a rotation of the shaft in one direction and, as far as possible, immediate clamping if a torque is exerted with the transmission element in the opposite direction, as a result of which a relative movement between the shaft and the sleeve is prevented.

Such a clamping freewheel has been disclosed by DE 605 879 as an overrunning clutch for motor vehicles and by AT 125 797 as a clutch for speed-change gearing.

Furthermore, DE 874 684 discloses an engaging and disengaging shaft coupling in which the force transmission is effected via balls which can bear against sloping running surfaces of the driving and driven shafts, an axial displacement of the shafts relative to one another leading to clamping of the balls, which transmits the torque. A similar solution in which the driving effect of balls is achieved by an axial displacement with conical running surfaces has been disclosed by JP 2004 125 140 A.

U.S. Pat. No. 3,279,571 discloses a coupling arrangement in which a drive shaft is connected in a rotationally locked manner to an axially conically tapering cylinder, the lateral surfaces of which form running surfaces of balls. By an axial movement of the shafts relative to one another, the balls are pressed outward in the chambers of the driven shaft and come into engagement with a chamber wall which is designed in such a way that driving is effected in one direction and freewheeling is effected in the other direction. In this case, the wall of the chamber in the driven shaft can taper in order thus to produce a clamping effect in one direction of rotation with a ball running in the chamber, whereas the ball runs freely in the other direction of rotation. By means of an axial rotation, a driving function of the balls can be disengaged with the conical cylinder of the driving wheel.

Furthermore, WO 99/04 178 discloses the use of cylindrical rollers as transmission element for a freewheel ratchet device.

One field of application of such a clamping freewheel is its use in a shuttle lock in prostheses. Stump transitions consisting of a soft elastomer, a "liner", are being increasingly used as an embedding layer between a prosthesis shank and the amputated stump. To fix the liner on the prosthesis shank, said liner is provided at the distal end with a fixed cap having a screwed-in pin. The pin has encircling grooves which interact with a gear as a transition element of the clamping freewheel, the shaft of the clamping freewheel lying perpendicularly to the longitudinal axis of the pin. The end of the liner can therefore only be displaced distally, whereas a return movement is prevented by the clamping freewheel. To release the locking, the freewheel shaft is axially displaced, as a result of which the gear is axially disengaged from the pin, so that the pin can be retracted. The known clamping freewheels of this type are constructed with needle rollers, which can readily be achieved in a small space. In practice, however, it is found that considerable clamping forces occur in the locked state of the clamping freewheel and these clamping forces impair the axial displacement of the shaft in the freewheel. The forces to be applied at the actuating element for the axial displacement may therefore become so large that requisite release of the locking by the patient cannot be effected. The causes of this may be an inadequate fit of the shank, as a result of which the distal liner plate in the prosthesis shank may become distorted. In the seat, the release force for releasing the locking may again increase to a marked extent due to the lever effect of the stump.

The object of the present invention is therefore to produce an improved clamping freewheel of the type mentioned at the beginning, which reduces the force for axially displacing the transmission element arranged on the shaft.

According to the invention, to achieve this object, a clamping freewheel of the type mentioned at the beginning is distinguished by the fact that the shaft consists of a hollow shaft piece and an inner piece axially displaceable therein, but mounted in a rotationally locked manner, and that the actuating element and the transmission element are arranged on the inner piece.

In the clamping freewheel according to the invention, the shaft is therefore of two-piece design, as a result of which the functions "axial displacement" and "clamping" are separated. The actual freewheel function is realized on the outside of the hollow shaft piece in conjunction with the sleeve, whereas the axial displacement is carried out on the inner piece relative to the hollow shaft piece. This achieves the effect that the axial displacement is virtually independent of the clamping forces which occur during the locking of the freewheel. When the clamping freewheel is used for locking a prosthetics part, it is thus ensured that the unlocking by the patient can be effected with essentially uniform unlocking forces. Impairment of or risks to the patient due to a freewheel which is difficult to release can therefore be avoided.

The anti-rotation locking between the hollow shaft piece and the inner piece can be effected by both the hollow shaft piece and the inner piece being of profiled design deviating from a circumference of a circle, the hollow shaft piece having an inner profile complementary to the outer profile of the inner piece. The inner piece may have, for example, a polygonal outer circumference. However, the anti-rotation locking may also be ensured in another manner, for example by a feather key.

In a further preferred embodiment, the inner piece, for the axial displacement, is mounted on the hollow shaft piece by means of balls. The ball mounting can be used for achieving the anti-rotation locking by at least one ball being arranged in at least one linear guide.

The preferred use of the clamping freewheel according to the invention is for locking a linearly movable prosthetic part, the movement of which can be transmitted to the clamping freewheel by means of a coupling element interacting with the transmission element of the freewheel, it being possible for the transmission element and the coupling element to be disengaged by the axial displacement of the inner piece of the shaft.

Figure 4:
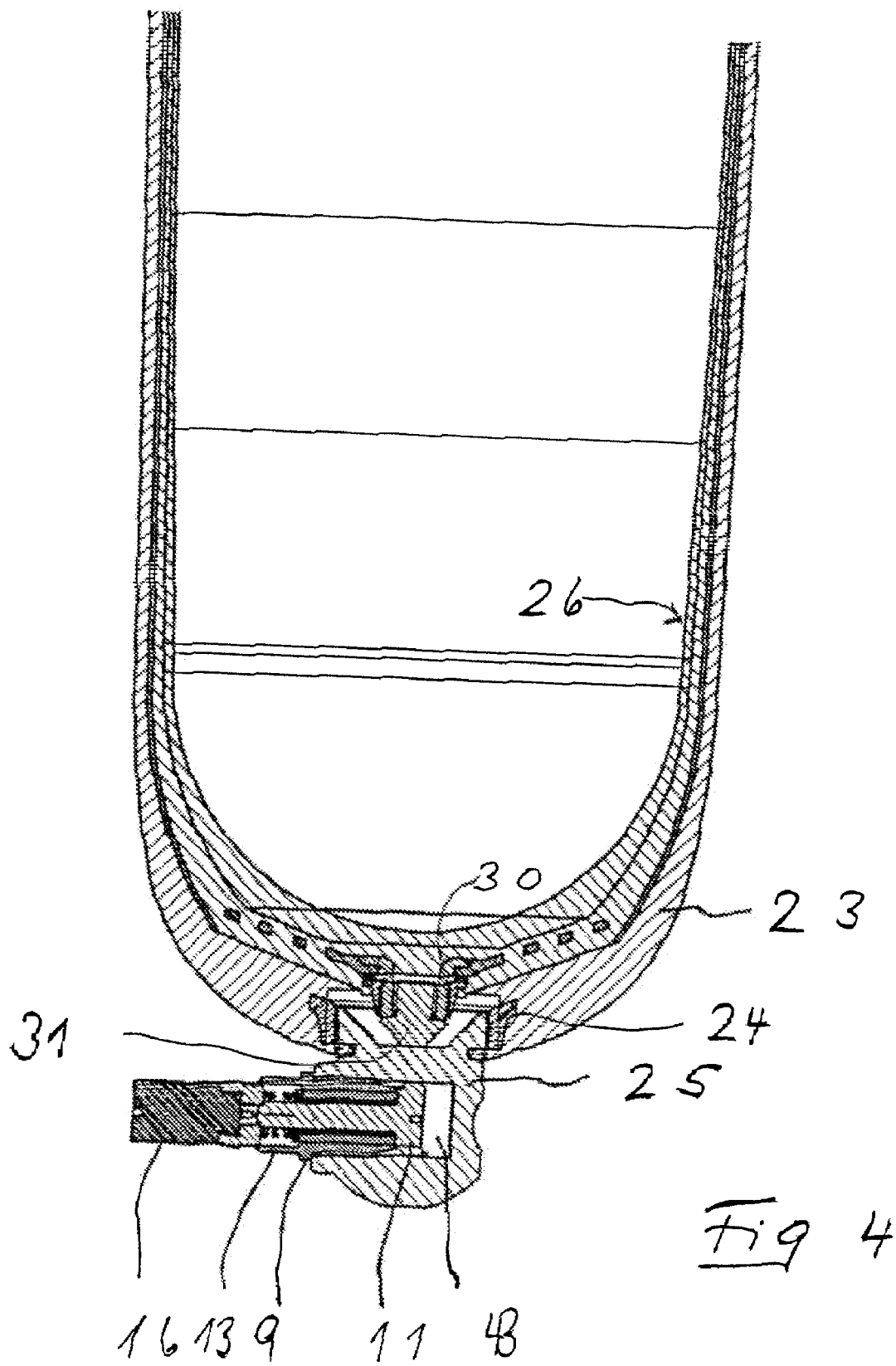

The invention is to be explained in more detail below with reference to an exemplary embodiment shown in the drawing, in which:

FIG. 1 shows an exploded illustration of a clamping freewheel according to the invention, FIG. 2 shows a sectional illustration of the assembled clamping freewheel according to FIG. 1, FIG. 3 shows a schematic vertical section through a shuttle lock for a prosthetic part with a clamping freewheel according to FIG. 1, FIG. 4 shows a vertical section in a plane rotated by 90° relative to FIG. 3.

The freewheel shown in FIGS. 1 and 2 has a hollow-cylindrical housing 1 which is shaped as a hexagon 3 on one side of an annular shoulder 2 and has an external thread 4 on the other side. Inserted into the housing 1 is a sleeve 5 which has chambers on its inner wall, needle bearings 6 (FIG. 2) being mounted in said sleeve 5 as rolling elements of a freewheel known per se. The sleeve 5 forms the freewheel together with the outer wall of a hollow shaft piece 7 which can be inserted into the bush in a matching manner. The hollow shaft piece 7 has an inner profile 8 in the form of a square, into which an inner piece 9 having a corresponding square outer profile 10 is inserted in a rotationally fixed manner. The push-in movement of the inner piece 9 into the inner profile 8 of the hollow shaft piece 7 is limited by a gear 11 which is arranged on the end of the inner piece 9, the outside diameter of the teeth and the inside diameter of the groove roots of said gear 11 being greater than the outside diameter of the hollow shaft piece 7.

The other end of the housing 1 is fitted with an annular stop disk 12 of a helical spring, used as a compression spring 13, and with a head piece 14 which can be rotatably inserted into the housing 1. The head piece 14 is connected to an extension piece 15 of the inner piece 9 in a rotationally fixed manner by an interference fit, a snap connection or a screwed connection. A rotary knob 16 can be snapped into place in the head piece 14 as actuating element by means of a latching groove 17 and a latching bead 18, the head piece 14 having a latching groove 19 of corresponding complementary design and a latching bead 20.

As FIG. 2 illustrates, an annular, axially extended chamber 21 is provided in the housing 1 above the sleeve 5 pressed into the housing 1, the compression spring 13 and the head piece 14 being accommodated in this chamber 21. The head piece 14 can be displaced axially into the interior of the housing against the restoring force of the compression spring 13 until a margin 22, projecting in an encircling manner, of the head piece 14 strikes the margin of the housing 1 and thus limits the push-in movement.

The push-in movement of the head piece 14, initiated at the actuating element 16, leads to a corresponding axial displacement of the gear 11, serving as transmission element, in order to disengage the latter from an associated coupling element, for example a longitudinally displaceable pin which is oriented with its longitudinal axis perpendicularly to the drawing plane in the illustration in FIG. 2 and is provided with corresponding grooves.

It can be seen that the axial displacement of the gear 11 is effected by a displacement of the inner piece 9 relative to the hollow shaft piece 7, whereas the clamping effect is effected by the rolling elements, designed as needle rollers in the exemplary embodiment shown, between the outer wall of the hollow shaft piece 7 and the inner wall of the sleeve 5, so that the axial displacement is independent of the clamping of the needle rollers 6.

FIGS. 3 and 4 show a prosthesis shank 23 designed in a funnel shape in a conventional manner and having a distal end which is closed in a pot-like manner and into which a shank adapter 24 is inserted, the latter serving to fasten a shuttle lock housing 25. An amputation stump is connected to the prosthesis shank 23 via a liner 26 which is pulled over the amputation stump and consists of a soft inner material 27 kind to the skin and of an outer material 28 which is preferably formed with a slidable surface and is provided with fabric reinforcement 29 in the region of the closed distal end. At the distal end, the liner 26 has a central screw sleeve 30, into which a locking pin 31 having an external thread is screwed. The locking pin is designed as an elongated bolt which is provided with radially encircling grooves 32 parallel to one another. The locking pin 31 is displaceably guided in the axial direction in a guide bore 31' of the shuttle lock housing 25. Furthermore, the shuttle lock housing 25 has a horizontal bore 33, into which the clamping freewheel described with respect to FIGS. 1 and 2 is inserted in such a way that the gear 11 engages in the grooves 32 of the locking pin 31 in the operating state, as shown in FIG. 3. The effect of the clamping freewheel is such that the locking pin 31 can be displaced in the distal direction by pressure on the liner 26, whereas retraction in the proximal direction is prevented by the clamping freewheel.

FIG. 4 shows a section along a vertical plane which is rotated by 90° relative to the section plane of FIG. 3 and is swung laterally in the region of the clamping freewheel, so that the section passes centrally through the horizontal bore 33 and the clamping freewheel. It can be seen that the inner piece 9 of the clamping freewheel with the gear 11 at the end is mounted in a chamber 34, which enables the inner piece 9 to be pressed in by means of the rotary knob 16 to such an extent that the gear 11 is disengaged from the grooves 32 of the locking pin 31, so that the locking pin 31 is released by the rotary knob 16 being pressed in and can thus be pulled upward out of its guide bore 31' in the shuttle lock housing 25. On account of the described design according to the invention, the unlocking is possible without any problems independently of the clamping forces applied by the needle cylinders 6 and thus also in the clamped state.

The invention claimed is:

1. A clamping freewheel having a sleeve (5) which encloses a shaft (7, 9) and in which the shaft (7, 9) is mounted in an axially displaceable manner, having rolling elements (6) which are arranged in chambers formed between shaft (7, 9) and sleeve (5) in such a way that said rolling elements roll in a first direction for a relative rotation between shaft (7, 9) and sleeve (5), whereas a torque acting in the opposite direction leads to the clamping of the rolling elements (6) in their chamber, said clamping freewheel further having a transmission element (11) arranged on the shaft (7, 9) and having an actuating element (16) for the axial displacement of the transmission element (11) arranged on the shaft (7, 9), wherein the shaft (7, 9) comprises a hollow shaft piece (7) and an inner piece (9) axially displaceable therein, but mounted in a rotationally locked manner, and wherein the actuating element (16) and the transmission element (11) are arranged on the inner piece (9), wherein the inner piece (9) is of a profiled design which deviates from the circumference of a circle and the hollow shaft piece (7) has a complementary inner profile (8) to said profiled design of said inner piece (9) whereby the inner piece (9) and the hollow shaft piece (7) are rotationally locked and whereby axial displacement of said inner piece (9) is made independent of said clamping of said rolling elements.

2. The clamping freewheel as claimed in claim 1, wherein the axial displacement of the inner piece (9) is effected against the restoring force of a spring (13).

3. The clamping freewheel as claimed in claim 1, wherein the transmission element is a gear.

4. The clamping freewheel of claim 1 wherein said profiled design is polygonal.

5. A prosthetic device comprising a prosthesis shank (23) including a liner (26) and a locking pin (31), and a clamping freewheel engaging said locking pin through a transmission element (11), said clamping freewheel having a sleeve (5) which encloses a shaft (7, 9) and in which the shaft (7, 9) is mounted in an axially displaceable manner, having rolling elements (6) which are arranged in chambers formed between shaft (7, 9) and sleeve (5) in such a way that said rolling elements roll in a first direction for a relative rotation between shaft (7, 9) an sleeve (5), whereas a torque acting in the opposite direction leads to the clamping of the rolling elements (6) in their chamber, wherein said transmission element (11) of said clamping freewheel is arranged on the shaft (7, 9) and having an actuating element (16) for the axial displacement of the transmission element (11) arranged on the shaft (7, 9), wherein the shaft (7, 9) comprises a hollow shaft piece (7) and an inner piece (9) axially displaceable therein, but mounted in a rotationally locked manner, and wherein the actuating element (16) and the transmission element (11) are arranged on the inner piece (9), wherein the inner piece (9) is of a profiled design which deviates from the circumference of a circle and the hollow shaft piece (7) has a complementary inner profile (8) to said profiled design of said inner piece (9) whereby the inner piece (9) and the hollow shaft piece (7) are rotationally locked and whereby axial displacement of said inner piece (9) is made independent of said clamping of said rolling elements.

6. The prosthetic device as claimed in claim 5, wherein the axial displacement of the inner piece (9) is effected against the restoring force of a spring (13).

7. The prosthetic device as claimed in claim 5, wherein the transmission element is a gear.

8. The prosthetic device of claim 5 wherein said profiled design is polygonal.

* * * * *